(12) United States Patent
Chaubron

(10) Patent No.: US 8,993,333 B2
(45) Date of Patent: *Mar. 31, 2015

(54) METHOD OF EVALUATING CANCER RISK IN HUMAN

(75) Inventor: Franck Chaubron, Venelles (FR)

(73) Assignee: Institut Clinident, Saint Beauzire (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/388,764

(22) PCT Filed: Aug. 3, 2010

(86) PCT No.: PCT/EP2010/061308
§ 371 (c)(1),
(2), (4) Date: Feb. 3, 2012

(87) PCT Pub. No.: WO2011/015589
PCT Pub. Date: Feb. 10, 2011

(65) Prior Publication Data
US 2012/0126111 A1 May 24, 2012

Related U.S. Application Data

(60) Provisional application No. 61/213,961, filed on Aug. 3, 2009.

(51) Int. Cl.
G01N 33/48 (2006.01)
G01N 1/18 (2006.01)
G01N 33/574 (2006.01)

(52) U.S. Cl.
CPC .... *G01N 33/57407* (2013.01); *G01N 33/57488* (2013.01)

USPC ............. 436/64; 436/63; 436/161; 436/173; 436/176; 436/178; 436/181; 250/282

(58) Field of Classification Search
CPC ............. G01N 33/48; G01N 33/497; G01N 33/57407; G01N 33/57423; G01N 33/57488; G01N 1/10; G01N 1/28; G01N 2560/00; G01N 2800/00; G01N 2800/18; G01N 2800/50; G01N 2800/60
USPC ............ 436/63, 64, 161, 173, 174, 176, 177, 436/178, 181; 422/68.1, 83, 89; 250/282
See application file for complete search history.

(56) References Cited

U.S. PATENT DOCUMENTS

| | | | |
|---|---|---|---|
| 6,723,501 B2 * | 4/2004 | Sakurai et al. | 435/4 |
| 6,759,010 B2 * | 7/2004 | Lewis et al. | 422/82.02 |
| 2005/0106642 A1 * | 5/2005 | Lipps et al. | 435/7.23 |
| 2006/0073538 A1 * | 4/2006 | Konrad | 435/18 |
| 2010/0210023 A1 * | 8/2010 | Wong et al. | 436/90 |
| 2010/0312133 A1 * | 12/2010 | Bazemore et al. | 600/532 |

OTHER PUBLICATIONS

Zlatkis et al. Analyst, vol. 106, 1981, pp. 352-360.*

* cited by examiner

*Primary Examiner* — Maureen Wallenhorst
(74) *Attorney, Agent, or Firm* — Young & Thompson

(57) ABSTRACT

Disclosed is a method of providing a risk evaluation and diagnosis of human cancer, by examining the presence, in the volatile fraction of a human saliva sample, of a combination of particulate biochemical volatile organic compounds, which is indicative of an increased risk of developing cancer.

10 Claims, 1 Drawing Sheet

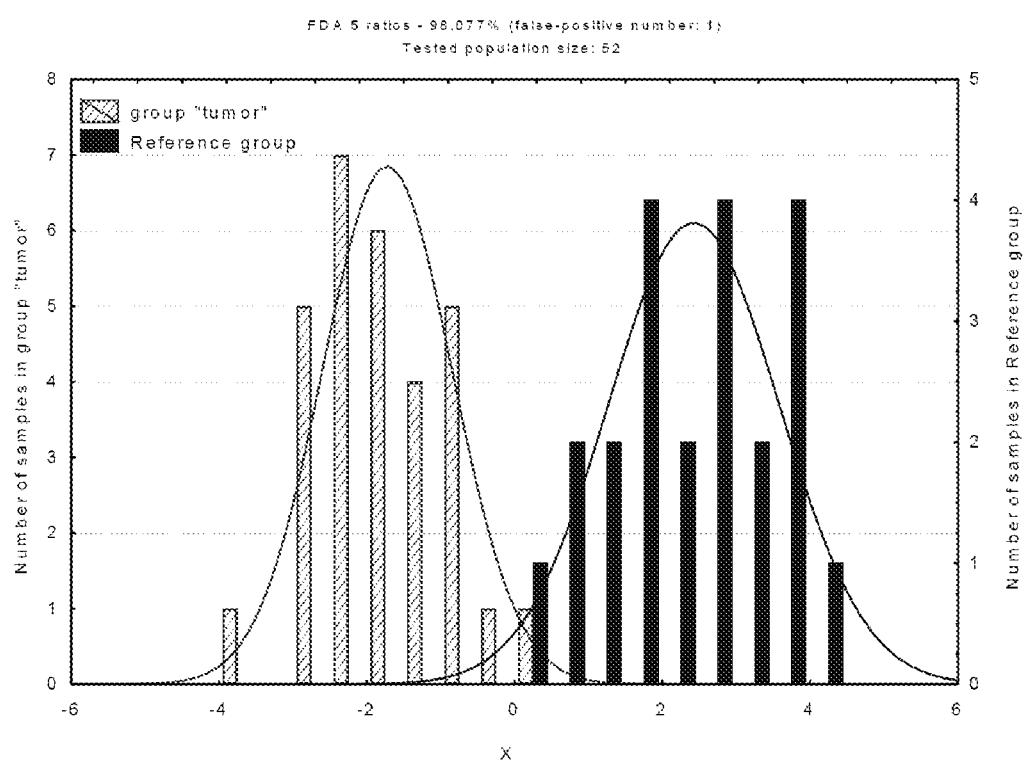

METHOD OF EVALUATING CANCER RISK IN HUMAN

The present invention relates to a method of providing a risk evaluation and diagnosis of human cancer by examining, in the volatile fraction of the saliva sample of a human subject, the presence of volatile biochemical organic compounds, a combination of which being indicative of an increased risk of cancer.

BACKGROUND OF THE INVENTION

Cancer is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

Cancer may affect people at all ages, even fetuses, but the risk for most varieties increases with age. Cancer causes about 13% of all human deaths. According to the American Cancer Society, 7.6 million people died from cancer in the world during 2007. Cancers can affect all animals.

Nearly all cancers are caused by abnormalities in the genetic material of the transformed cells. These abnormalities may be due to the effects of carcinogens, such as tobacco smoke, radiation, chemicals, or infectious agents. Other cancer-promoting genetic abnormalities may be randomly acquired through errors in DNA replication, or are inherited, and thus present in all cells from birth. The heritability of cancers are usually affected by complex interactions between carcinogens and the host's genome. New aspects of the genetics of cancer pathogenesis, such as DNA methylation, and microRNAs are increasingly recognized as important.

Most cancers are initially recognized either because signs or symptoms appear or through screening. Neither of these lead to a definitive diagnosis, which usually requires the opinion of a pathologist, a type of physician (medical doctor) who specializes in the diagnosis of cancer and other diseases.

People with suspected cancer are investigated with medical tests. These commonly include blood tests, X-rays, CT scans and endoscopy. A cancer may be suspected for a variety of reasons, but the definitive diagnosis of most malignancies must be confirmed by histological examination of the cancerous cells by a pathologist. Tissue can be obtained from a biopsy or surgery. Many biopsies (such as those of the skin, breast or liver) can be done in a doctor's office. Biopsies of other organs are performed under anesthesia and require surgery in an operating room.

The existing diagnostic tests for cancer are thus often unpleasant for the patient and may be risky for the health (X-ray, surgery . . . ). There is therefore a need for a non invasive and reliable diagnostic test of cancer, that can be performed routinely and in the usual practice or laboratories.

The present invention disclosed a reliable and sensitive diagnostic method applied to the saliva of human subjects.

Saliva is a clear, slightly acidic fluid that contains a number of inorganic and organic constituents important to oral health. Whole saliva is a mix of secretions from major and minor salivary glands and gingival crevicular fluid, which contains sloughed host cells, bacteria and food debris. Therefore, saliva is not a passive "ultrafiltrate" of serum, but contains a distinctive composition of enzymes, hormones, antibodies, and other molecules (Rehak, N. N. et al. 2000 Clin Chem Lab Med 38:335-343; Wong D T, American Scientist, vol 96, 2008). For example, saliva contains a large number of proteins that aid in the protection of oral cavity tissues, including mucins, amylases, agglutinins, lisozymes, peroxidases, lactoferrin and secretory IgA. Whole saliva contains normal epithelial cells and leukocytes that can be pelleted, and from which one can easily recover genomic DNA and mRNA, potentially used to find genomic markers of several diseases. Indeed, most of the DNA or RNA extracted from crude saliva was found to be of viral or bacterial origin (Stamey, F. R. et al. 2003 J Virol Methods 108:189-193; Mercer, D. K. et al. 2001 FEMS Microbiol Lett 200:163-167) and of human extra or intracellular origin. Also, many groups have focused their study and diagnostic tests on the supernatant and thus cell-free phase of whole saliva, which contains many analytes such as free mRNA (Zimmermann B G et al, Oral Oncology 2008, 44, 425-429).

In the past 10 years, the use of saliva as been successfully applied in diagnostics (Streckfus, C F. & Bigler, L. R. 2002 Oral Dis 8:69-76). Diagnostic biomarkers in saliva have been identified for monitoring caries, periodontitis, salivary gland diseases, and systemic disorders, e.g., hepatitis and HIV (Lawrence H. P. et al, 2002 J Can Dent Assoc 68: 170-174). Also, oral bacteria have been reported to be elevated in oral and esophageal cancer lesions (Mager D. L. et al. J Transl Med. 2005; 3: 27, Hooper J. S et al., Journal of Clinical Microbiology, May 2006, P 1719-1725). The reason for these shifts in bacterial colonization of cancer lesions is unclear. Mechanistic studies of bacterial attachment provide some insights and research has repeatedly shown that oral bacteria demonstrate specific tropisms toward different biological surfaces in the oral cavity such as the teeth, mucosa, and other bacteria. There is less time in oral cavity, for a complex biofilm to develop on soft tissue surfaces; thus, a premium is placed on potent mechanisms of adhesion. The differences in bacterial tropisms for specific oral sites suggest that different intra-oral surfaces and bacterial species have different receptors and adhesion molecules that dictate the colonization of different oral surfaces. Certain glycoconjugates serve as receptors for specific bacteria and recent reports support the notion that shifts in the colonization of different cancer cells are associated with observed changes in cell surface receptors. Hence, Mager D. L. et al showed that the salivary microbiota in subjects with an oral squamous cell carcinoma (OSCC) lesion differs from that found in OSCC-free controls. Bacterial counts were determined for each species, averaged across subjects in the 2 subject groups, and significance of differences between groups determined using the Mann-Whitney test and adjusted for multiple comparisons; interestingly, it appeared that the bacteria strains *Capnocytophaga gingivalis, Prevotella melaninogenica, Streptococcus mitis* and *Micrococcus luteus* were particularly present in patients having OSCC and were therefore suggested to serve as diagnostic markers for oral cancer. However, as it is demonstrated in (ref), these particulate bacteria strains were poorly associated with oral cancer (a maximal sensitivity of 80%) (Mager D. L. et al). Also, it has been shown in Li et al (Journal of Applied Microbiology, 2004, 97, 1311-1318) that the presence in saliva of significant high numbers of specific alive bacteria (40 different strains have been identified in this study and more than 200 specific alive bacteria have been described in the oral cavity), could be associated to the biofilm formation, colonization of the oral cavity and lack of oral hygiene that are often associated to oral cancer development in developing countries. However, one can not predict from Li et al that the particulate strains *Capnocytophaga gingivalis, Pre-*

*votella melaninogenica*, *Streptococcus mitis* and *Micrococcus luteus* can serve as reliable diagnostic markers for human oral cancer.

Interestingly, the use of the saliva has never been proposed for a diagnostic test intended to detect human cancer.

Saliva is a mixture of secretions from multiple salivary glands, including the parotid, submandibular, sublingual and other minor glands lying beneath the oral mucosa. As mentioned before, human saliva harbors a wide spectrum of peptides and proteins that constitutes the human salivary proteome. What has been less studied is the presence of organic biochemical compounds in the saliva.

Biochemical organic compounds can be enzymes, hormones, inorganic ions, peptides, proteins, carbohydrates, vitamins, lipids, fatty acids and volatile compounds. They can be measured by many techniques and devices, either optical technologies (for example laser absorption spectroscopy, mid infra red absorption spectroscopy, laser magnetic resonance spectroscopy, proton transfer reaction mass spectrometry . . . ) or non-optical technologies (gas chromatography, mass spectrometry, etc. . . . ) (Mashir A, Advanced Powder Technology, 2009).

Only one study has ever compared the biochemical organic content of a fraction of saliva from healthy or sick-patients (Volozhin et al. Stomatologiia (mosk), 2001; 80(1):9-12). In this study, patients with chronic generalized periodontitis and patients with chronic generalized gingivitis and periodontitis have been tested with air from the oral cavity and liquid samples were collected by washing the oral cavity with sterile water. Chemical compounds of the air and the washed liquid were analyzed by chromato-mass-spectrometry, gas-adsorption and gas-liquid chromatography. The content of dimethyl sulphide, dimethyl disulphide increased in the oral air and such volatile short chain fatty acids (VSCFA) as butyrate, propionate, acetate rose, but their aldehydes (butyraldehyde, acrolein, acetaldehyde) decreased in oral fluid during periodontitis. It was also shown that volatile short-chain fatty acids (propionate, butyrate and acetate) of bacterial and tissue origin are important factors of pathogenesis of oral tissue inflammation (Volozhin et al. Stomatologiia (mosk), 2001; 80(1):9-12). In this study, the organic compounds have been analyzed in air from the oral cavity and rincing liquid collected by washing the oral cavity with sterile water but not in the volatile fraction of the raw saliva.

Contrary to saliva, the presence of volatile organic molecules in exhaled breath has been well studied and was shown to contain a lot of biochemical organic compounds: in 1971, using gas-liquid partition chromatography analysis, Linus Pauling demonstrated the presence of 250 substances in exhaled breath (Pauling L. et al. Proc. Natl. Acad. Sci. USA 68 (1971) 2374-2376). In 1990, the development of very sensitive modern mass spectrometry (MS) and gas chromatography mass spectrometry (GC-MS) instruments, gives identity to thousands of unique substances in human exhaled breath (Mashir A, Advanced Powder Technology, 2009). These substances include elemental gases like nitric oxide and carbon monoxide and a multitude of other volatile organic compounds. Furthermore, exhaled breath also carries aerosolized droplets collected as exhaled breath condensate that have non-volatile compounds that can be captured by a variety of methods and analyzed for a wide range of biomarkers from metabolic end products to proteins. Breath analysis is now used to diagnose and monitor asthma, pulmonary hypertension, respiratory diseases, gastrointestinal diseases, critical illness, to check for transplant organ rejection, and to detect lung cancer, and breast cancer (Mashir A, Advanced Powder Technology, 2009; Chan H. P. et al, Lung Cancer, 2009). However, it is noteworthy that breath analysis has never been proposed to detect oral cancer in human subject.

Interestingly, it appeared that the biochemical organic molecular composition of saliva has never been compared between patients suffering from cancer and healthy individuals. Moreover, the biochemical organic molecular composition of the volatile fraction of saliva has never been studied so far to detect epithelial cancer, non-epithelial cancer, as well as those of solid and non-solid cancers. Cancers consisting of epithelial cancer cells include, for example, lung cancer, breast cancer, gastric cancer, colorectal cancer, uterine cervical cancer, uterine cancer, oral cancers, i.e. cancer of the oral cavity (e.g., laryngeal cancer, pharyngeal cancer, lingual cancer, etc.), cancer of the oropharynx, oropharyngeal squamous cell carcinoma (OSCC), or head and neck squamous cell carcinoma, prostate cancer, colon cancer, squamous cell carcinoma, including, adenocarcinoma and the like; cancers consisting of aforementioned non-epithelial cancer cells (sarcoma) include, for example, liposarcoma, osteosarcoma, chondrosarcoma, rhabdomyosarcoma, leiomyosarcoma, fibrosarcoma, angiosarcoma, and the like.

The volatile fraction corresponds to the evaporated part of the fluid fraction of saliva. This volatile fraction contains some organic compounds that are not found in the raw saliva sample without the evaporation process, even after its filtration.

Also, it is important to note that the molecular content of saliva is not comparable at all to the composition of exhaled breath, which is mostly a reflect of lung molecules (Song G, et al. Quantitative breath analysis of volatile organic compounds of lung cancer patients, Lung Cancer (2009)). Hence, the molecular composition of the volatile fraction of saliva can not be inferred from the data issued from the breath analysis. To date, no exhaustive analysis of the biochemical content of the volatile fraction of saliva has never been disclosed, a fortiori in the context of cancer.

One of the values of saliva is the ease of sampling and subject compliance for sample collection, which includes field applications as well as home collection. However, the study of the biochemical compounds present in saliva (either in fluid or in the volatile fraction) for clinical application appeared to be difficult since it is necessary to stabilize and maintain their integrity for at least several days at room temperature.

It has already been shown that the RNAprotect® Saliva reagent (RPS, Qiagen Inc, Valencia, Calif.) could stabilize RNA in samples at room temperature for up to 12 weeks (Park N J, Clin Chem 2006; 52:2303-4). Also, Jiang J et al showed that it is possible to use the RPS for stabilization of DNA and proteins in saliva only when endogenous cells are previously removed by centrifugation or by filtration (Jiang J et al, Archives of Oral Biology, 2008).

However, as far as biochemical organic compounds are concerned, they are degraded by the microflora, food and dental care products at room temperature. Importantly, nobody has ever proposed a way to protect these sensitive compounds from the degradation occurring at room temperature.

Therefore, it is still a major challenge to stabilize all the components of saliva, especially organic compounds, without any filtration or centrifugation steps, for a long time at room temperature.

In this context, the present inventors show here for the first time that:
 i) it is possible to stabilize organic compounds present in saliva during at least 10 days in an appropriate buffer, ii) it is possible to extract a volatile fraction from a sample of stabilized saliva, and to detect therein several organic volatile compounds in a significant amount, iii) it is possible to detect a high risk of developing cancer by analyzing the level of only few particular biochemical compounds in said volatile fraction of stabilized saliva.

Importantly, it is to note that no test for predicting and/or diagnosing cancer using the volatile fraction of saliva has ever been proposed so far.

More importantly, the particular biochemical compounds hereafter identified have never been associated with cancer so far.

The present invention therefore discloses:

i) a method for stabilizing crude saliva samples of human subjects, ii) a method for extracting the volatile fraction of stabilized saliva samples, and to analyze its content in biochemical organic compounds, iii) a method for detecting a high risk of developing cancer, by analyzing the level of particular organic biochemical compounds in the volatile fraction of stabilized saliva.

Finally, specific combinations of biological parameters associated with high risk of cancer have been identified, highlighting that it is possible to obtain a reliable and sensitive prognosis/diagnosis test of cancer from a unique sample of stabilized saliva.

FIGURE DESCRIPTION

FIG. 1 shows an histogram representing the 2 groups of saliva samples after a Factorial Discriminant Analysis (FDA) on ratios data according to the factor <<tumor/healthy>>: 5 ratios allow to separate 98.077% of the samples in the 2 groups <<tumor>> and <<reference group>> (only 1 reference sample is classified in the group <<tumor>> and not in the reference group).

DESCRIPTION

The present invention disclose a new reliable, sensitive and easy to handle diagnostic test of cancer in human subject.

The present invention enables to diagnose a cancer in a human subject. As a matter of fact, the present invention disclosed an in vitro method of diagnosing a cancer in a human subject, comprising stabilizing a crude saliva sample from said human subject, and analyzing the volatile fraction extracted from said stabilized saliva, wherein the detection of at least one biochemical organic compound in said volatile fraction is indicative of a risk of developing a cancer.

The method of the invention is thus dedicated to estimate a risk for a human subject of developing a cancer. This risk can be either a high risk of developing a cancer or a low risk of developing a cancer.

As used herein, when a human subject has a risk "of developing" a cancer, it means that he has a risk "to be developing" a cancer at the time of the collection of the saliva sample.

In the context of the invention, a human subject is said "to have a high risk of developing a cancer" when he has a risk superior 70%, preferably 80%, more preferably 90% and even more preferably 95% of developing cancer. In other words, the human subject has a higher probability to develop cancer as compared to the normal population or to a human subject in which none of the organic compound is detected. In the context of the present invention, when a human subject has a risk superior to 97% to be developing a cancer, it is said that the human subject "is developing a cancer".

This cancer can be initiating or well-established. In one embodiment of the invention, the level of expression of particulate biochemical organic compounds can potentially indicate the grade of the cancer from which the human subject is suffering.

The method of the invention also enables to determine if a human subject has a low risk to be developing a cancer. In the context of the invention, the human subject has a low risk of developing cancer when he has a risk of developing cancer lower than 10%, preferably lower than 5% as compared with the normal population. In other words, the human subject has a chance superior to 90%, preferably 95% to be healthy, at least as far as cancer is concerned. In the context of the invention, when a human subject has a risk inferior to 5% of being developing a cancer, it is said that the human subject is not developing a cancer at the time of the collection of the saliva sample.

The present invention also contemplates a method of diagnosing a predisposition to cancer in a human subject, the method comprising stabilizing a crude saliva sample from said human subject, analyzing the volatile fraction extracted from said stabilized saliva, wherein the detection in said volatile fraction of at least one biochemical organic compound is indicative of either a predisposition to cancer or no predisposition to cancer.

When a human subject is said to have "a predisposition to cancer", it means that he has a risk superior 70%, preferably 80%, more preferably 90% and even more preferably 95% of developing cancer in a short or far future as compared to the mean healthy population. This cancer predisposition is generally linked to a genetic cause.

When a human subject is said "not to be predisposed to cancer", it means that he has a risk inferior to 10%, preferably 5% of developing cancer in a short or far future as compared to the mean healthy population. It generally means that he has at least 90% of chance not to have oncogenic mutations in his genome.

There is no particular limitation regarding the types of cancer which can be identified by the method according to the present invention: they include epithelial cancer, non-epithelial cancer, as well as those of solid and non-solid cancers. Cancers consisting of epithelial cancer cells include, for example, lung cancer, breast cancer, gastric cancer, colorectal cancer, uterine cervical cancer, uterine cancer, oral cancers, i.e. cancer of the oral cavity (e.g., laryngeal cancer, pharyngeal cancer, lingual cancer, etc.), cancer of the oropharynx, oropharyngeal squamous cell carcinoma (OSCC), or head and neck squamous cell carcinoma, prostate cancer, colon cancer, squamous cell carcinoma, including oral squamous cell carcinoma (OSCC), adenocarcinoma and the like; cancers consisting of aforementioned non-epithelial cancer cells (sarcoma) include, for example, liposarcoma, osteosarcoma, chondrosarcoma, rhabdomyosarcoma, leiomyosarcoma, fibrosarcoma, angiosarcoma, and the like. Other cancers also can be identified by the present invention, including, for example, basalioma, Merkel cell carcinoma, myxoma, non-small cell tumor, oat cell tumor, papilloma, bronchiolar tumor, bronchial tumor; leukemia such as B cell tumor, mixed cell tumor, null cell tumor, T cell tumor; HTLV-II related tumors such as lymphocytic acute leukemia, lymphocytic chronic tumor, mastocytoma, and myeloma; histiocytic malignant tumors such as Hodgkin's tumor, non-Hodgkin's lymphoma, malignant melanoma, mesothelioma, Ewing sarcoma, periosteoma, adenofibroma, adenolymphoma, craniopharyngioma, dysgerminoma, mesenchymoma, mesonephroma, ameloblastoma, cementoma, odontoma, thymoma, adenocarcinoma, cholangioma, cholesteatoma, cylindroma, cystic adenoma, cystic tumor, granulosa cell tumor, ovarian tumor, hepatic cancer, syringocarcinoma, islet cell tumor, Leydig cell tumor, Sertoli cell tumor, theca cell tumor, leiomyoma, myoblastoma, ependymoma, neural myoma, glioma, medulloblastoma, periosteoma, neurilemma, neuroblastoma, neuroepithelioma, neurofibroma, neuroma, paraganglioma, nonchromaffin paraganglioma, angiokeratoma, hematolymphangioma, sclerosing hemangioma, glomus tumor, angioendothelioma, lymphangioma, lymphangiomyoma, lymphagiosarcoma, pineocytoma, carcinosarcoma, colorectal sarcoma, neurofibroma and the like.

The present method may begin by collecting a crude saliva sample from the human subject. This is done by receiving, in a sterile device, a sample of the saliva that has been spitted by the human subject. A collecting reagent, for example a citrate buffer, may be added to the sample. This sample is then treated so as to stabilize it for later analysis, and to prepare it to volatile fraction extraction.

It is one aspect of the present invention to provide a method to stabilize crude samples of saliva, so as to maintain a high amount of biochemical organic compounds initially present in the spitted and collected saliva, that is preferably at least 70%, more preferably 80% and even more preferably 90% of the biochemical organic components initially present in the spitted and collected saliva. Interestingly, this method also enables to favour biochemical volatile elements extraction.

As a matter of fact, the method of the present invention enables to protect the raw components of the sample from degradation during at least 10 days at room temperature thanks to a stabilization step. This stabilization step is performed by adding to the crude sample a so-called "saliva preservation solution" comprising at least a preservation reagent, which is preferably a buffer comprising a salt capable of a) opening the membrane of bacteria and human cells, b) reducing the vapour tension of volatile compounds without allowing the degradation of said compounds. This salt is preferably a salt such as guanidinum thiocyanate, and/or ammonium sulfate and/or sodium azide, and more preferably is sodium azide. This salt is employed preferably at a concentration range between 20 mM and 6 M, and more preferably at 40 mM.

The present invention therefore discloses a method for stabilizing the raw components of a crude saliva sample (such as nucleic acid and biochemical organic compounds) during at least 10 days at room temperature, said method comprising adding to the crude saliva sample a salt such as guanidinum thiocyanate, and/or ammonium sulfate and/or sodium azide. The salt is preferably sodium azide and is present at a concentration of about 40 mM.

Therefore, as used herein, "stabilized" saliva sample designate samples in which organic volatile compounds have been preserved from degradation caused by the microflora, food and dental care products, during at least 10 days at room temperature.

In the context of the invention, the "volatile fraction" is recovered from the heating of a crude saliva sample. Preferably, said volatile fraction is extracted from crude saliva sample by heating said saliva sample for at least 10 minutes, preferably 20 minutes and more preferably 30 minutes at a temperature which is comprised between 30 and 50° C., and is preferably of about 40° C. During this time, the volatile fraction is taken away from the sample by using a solid-phase microextraction (SPME) with a carboxen/polydimethylsiloxane coated fiber (CAR/PDMS fiber). The desorption temperature of the fiber is comprised between 250° C. and 300° C., and is preferably of about 280° C.

Therefore, in one embodiment of the present invention, the volatile biochemical organic compounds are extracted with a CAR/PDMS fiber coating during at least, preferably 20 minutes, and even more preferably 30 minutes from a saliva sample that is simultaneously heated at a temperature comprised between 30° C. and 50° C., which is preferably of about 40° C.

Solid-phase microextraction (SPME) is a patented sample preparation technique based on the adsorption of analytes directly from an aqueous sample onto a coated, fused-silica fiber. This sampling technique is fast, easy to use and eliminates the use of organic solvents (Mills G et al, Journal of Chromatography 2000; Song C et al, Lung Cancer 2009).

In this technology, the CAR/PDMS fibers are often used for detecting trace level of volatile compounds, and are therefore well-known from the man skilled in the art (Garcia-Esteban M et al, Talanta 2004).

Preferably, the detection of said biochemical organic compound is performed by using a chromatograph in gas phase coupled to a mass spectrometer.

The term "detecting" as used herein is meant to refer to diagnosing, inferring, evaluating, monitoring, determining the amount, concentration, ratio, or other quantitative or qualitative assessment in samples, optionally compared to a control sample, of volatile compounds.

In the context of the invention, a biochemical compound is "detected" when the expression level of said compound is at least superior to 1.5 fold the mean expression level of said compound in the normal population.

In a particulate embodiment, the present invention is therefore drawn to a method of diagnosing a predisposition to cancer or diagnosing a cancer in a human subject, comprising the steps of:
   a) collecting a sample of crude saliva of said human subject in a sterile device,
   b) stabilizing said sample by adding a solution comprising a salt, such as guanidinum thiocyanate, ammonium sulfate and/or sodium azide,
   c) extracting the volatile fraction from said stabilized sample by heating it for at least 10 minutes at 40° C. and using for example Solid-phase Microextraction (SPME) to take away the volatile fraction,
   d) detecting at least one biochemical organic compound by using for example a chromatograph in gas phase coupled to a mass spectrometer, wherein the detection of at least one, preferably at least two, and more preferably at least three biochemical organic compound(s) is indicative of a risk or a predisposition to cancer.

From a chemistry point of view, biochemical organic compounds are the members of a large class of chemical compounds whose molecules contain carbon. They can be antigens, carbohydrates, enzymes, hormones, lipids, fatty acids, neurotransmitters, nucleic acids, proteins, peptides and amino acids, vitamins, fats and oils.

Among all the known organic compounds, "Volatile organic compounds" (VOC) are meant to designate any organic compound that is volatile, i.e. that have a high vapor pressure or low boiling point, and can therefore evaporate at normal temperature and pressure. These compounds are often regulated by governments. For example, in European Union, a "Volatile Organic Compound" is any organic compound having an initial boiling point less than or equal to 250° C. measured at a standard atmospheric pressure of 101.3 kPa.

By applying the method of the invention, some biochemical compounds were shown to be highly overexpressed in the volatile fraction of human subjects suffering from cancer and were therefore found to be acute and sensitive diagnostic and/or prognostic tool of cancer. Importantly, none of these compounds can be detected in the fluid fraction of saliva, highlighting the necessity to study the volatile fraction of saliva in this case.

In one embodiment of the present invention, the method of the invention is intended to diagnose epithelial cancer, non-epithelial cancer, as well as those of solid and non-solid cancers. Cancers consisting of epithelial cancer cells include, for example, lung cancer, breast cancer, gastric cancer, colorectal cancer, uterine cervical cancer, uterine cancer, oral cancers, i.e. cancer of the oral cavity (e.g., laryngeal cancer, pharyngeal cancer, lingual cancer, etc.), cancer of the oropharynx, oropharyngeal squamous cell carcinoma (OSCC), or head and neck squamous cell carcinoma, prostate cancer, colon cancer, squamous cell carcinoma, including oral squamous cell carcinoma (OSCC), adenocarcinoma and the like; cancers consisting of aforementioned non-epithelial cancer cells (sarcoma) include, for example, liposarcoma, osteosarcoma, chondrosarcoma, rhabdomyosarcoma, leiomyosarcoma, fibrosarcoma, angiosarcoma, and the like.

In addition, most of these cancers are initially asymptomatic and are not diagnosed or treated until they reach an advanced stage. As of today, patients are questioned about associated risk to cancer (smoker, alcohol) followed by clinical inspection.

In an embodiment, the present invention provides a method of diagnosing epithelial cancer, non-epithelial cancer, as well as those of solid and non-solid cancers in a human subject, by analyzing the content in biochemical compounds in the volatile fraction of stabilized samples of saliva, wherein the detection of at least one of the biochemical organic compound selected in the group consisting of: 2,3-pentanedione (CAS number 600-14-6), 3-methyltiophene (CAS number 616-44-4), acetone (CAS number 67-64-1), hexanenitrile (CAS number 628-73-9), benzaldehyde (CAS number 100-52-7), 3-methyl-2-pentanone (CAS number 565-61-7), 2,3-butanedione (CAS number 431-03-8), 2-propanol (CAS number 67-63-0), ethyl acetate (CAS number 141-78-6), 1-propanol (CAS number 71-23-8), hexanal (CAS number 66-25-1), 5-methyl-3-hexen-2-one (CAS number 5166-53-0), m-xylene (CAS number 108-38-3), p-xylene (CAS number 106-42-3), 2-methyl-2-butenal (E) (CAS number 497-03-0), phenol (CAS number 108-95-2), butanal (CAS number 123-72-8), methylbutanone (CAS number: 563-80-4), 2-methyl-2-butene (CAS number 513-35-9), 2-methyl-1-propene (CAS number 115-11-7), (cis) 1,2 dimethyl-cyclopropane (CAS number: 930-18-7) heptanal (CAS number 111-71-7), nonanal (CAS number 124-19-6), octanal (CAS number 124-13-0), cyclopentane methyl (CAS number 96-37-7), decane (CAS number 124-18-5), hexane (CAS number 110-54-3), nonane (CAS number 111-84-2), pentane 2,2,4-trimethyl (CAS number 540-84-1), benzene (CAS number 71-43-2), benzene ethyl (CAS number 100-41-4), styrene (CAS number 100-42-5), toluene (CAS number 108-88-3), butanoic acid 2-methyl-ethyl ester (CAS number 7452-79-1), 2-butanone (CAS number 78-93-3), 2-butanone 3-hydroxy (CAS number 513-86-0), acetophenone (CAS number 98-86-2), pentanal (CAS number 110-62-3), aniline (CAS number 62-53-3), furan 2-methyl (CAS number 534-22-5), decanal (CAS number 112-31-2), propanal 2-methyl (CAS number 78-84-2), butanal 3-methyl (CAS number 590-86-3), 2-propenal 2-methyl (CAS number 78-85-3), 1-butanol 3-methyl (CAS number 123-51-3), 2-butanol (CAS number 15892-23-6), 2,3-octanedione (CAS number 585-25-1), 2,3-pentanedione (CAS number 600-14-6), 2-octanone (CAS number 111-13-7), 2-heptanone (CAS number 110-43-0), 3-buten-2-one 3-methyl (CAS number 814-78-8), acetic acid (CAS number 64-19-7), butanoic acid 3-methyl-ethyl ester (CAS number 108-64-5), 1-hexene 3,5,5-trimethyl (CAS number 4316-65-8), 2-hexene 2,5,5-trimethyl (CAS number 40467-04-7), 1-propene 2-methyl (CAS number 115-11-7), methylcyclohexane (CAS number 108-87-2), cyclopropane 1,2-dimethyl (cis) (CAS number 930-18-7) is indicative of a risk of developing a cancer.

In a particular embodiment, the detection of at least one of the biochemical organic compound selected in the group consisting of: 2,3-pentanedione (CAS number 600-14-6), 3-methyltiophene (CAS number 616-44-4), acetone (CAS number 67-64-1), hexanenitrile (CAS number 628-73-9), benzaldehyde (CAS number 100-52-7), 3-methyl-2-pentanone (CAS number 565-61-7), 2,3-butanedione (CAS number 431-03-8), 2-propanol (CAS number 67-63-0), ethyl acetate (CAS number 141-78-6), 1-propanol (CAS number 71-23-8), hexanal (CAS number 66-25-1), 5-methyl-3-hexen-2-one (CAS number 5166-53-0), m-xylene (CAS number 108-38-3), p-xylene (CAS number 106-42-3), 2-methyl-2-butenal (E) (CAS number 497-03-0), phenol (CAS number 108-95-2), butanal (CAS number 123-72-8), methylbutanone (CAS number: 563-80-4), 2-methyl-2-butene (CAS number 513-35-9), 2-methyl-1-propene (CAS number 115-11-7), (cis) 1,2 dimethyl-cyclopropane (CAS number: 930-18-7) is indicative of a risk of developing a cancer, and preferably an oral cancer.

In another embodiment, the detection of at least one of the biochemical organic compound selected in the group consisting of: heptanal (CAS number 111-71-7), nonanal (CAS number 124-19-6), octanal (CAS number 124-13-0), cyclopentane methyl (CAS number 96-37-7), decane (CAS number 124-18-5), hexane (CAS number 110-54-3), nonane (CAS number 111-84-2), pentane 2,2,4-trimethyl (CAS number 540-84-1), benzene (CAS number 71-43-2), benzene ethyl (CAS number 100-41-4), styrene (CAS number 100-42-5), toluene (CAS number 108-88-3), butanoic acid 2-methyl-ethyl ester (CAS number 7452-79-1), 2-butanone (CAS number 78-93-3), 2-butanone 3-hydroxy (CAS number 513-86-0), acetophenone (CAS number 98-86-2), pentanal (CAS number 110-62-3), aniline (CAS number 62-53-3), furan 2-methyl (CAS number 534-22-5), decanal (CAS number 112-31-2), propanal 2-methyl (CAS number 78-84-2), butanal 3-methyl (CAS number 590-86-3), 2-propenal 2-methyl (CAS number 78-85-3), 1-butanol 3-methyl (CAS number 123-51-3), 2-butanol (CAS number 15892-23-6), 2,3-octanedione (CAS number 585-25-1), 2,3-pentanedione (CAS number 600-14-6), 2-octanone (CAS number 111-13-7), 2-heptanone (CAS number 110-43-0), 3-buten-2-one 3-methyl (CAS number 814-78-8), acetic acid (CAS number 64-19-7), butanoic acid 3-methyl-ethyl ester (CAS number 108-64-5), 1-hexene 3,5,5-trimethyl (CAS number 4316-65-8), 2-hexene 2,5,5-trimethyl (CAS number 40467-04-7), 1-propene 2-methyl (CAS number 115-11-7), methylcyclohexane (CAS number 108-87-2), cyclopropane 1,2-dimethyl (cis) (CAS number 930-18-7) is indicative of a risk of developing a cancer, and preferably a lung cancer.

This risk can be either a high risk, or a low risk of developing cancer.

Indeed, the below-presented results have shown that the detection of at least one, preferably two, more preferably three, and even more preferably four of the following compounds: 2,3-pentanedione (CAS number 600-14-6), 3-methyltiophene (CAS number 616-44-4), acetone (CAS number 67-64-1), hexanenitrile (CAS number 628-73-9), benzaldehyde (CAS number 100-52-7), 3-methyl-2-pentanone (CAS number 565-61-7), 2,3-butanedione (CAS number 431-03-

8), 2-propanol (CAS number 67-63-0), ethyl acetate (CAS number 141-78-6), 1-propanol (CAS number 71-23-8), hexanal (CAS number 66-25-1), 5-methyl-3-hexen-2-one (CAS number 5166-53-0), m-xylene (CAS number 108-38-3), p-xylene (CAS number 106-42-3), 2-methyl-2-butenal (E) (CAS number 497-03-0) in the volatile fraction of saliva of a human subject indicates that said human subject has a high risk of developing a cancer, and preferably an oral cancer. On the contrary, when at least one particulate biochemical organic compound as disclosed above is not detected in the saliva sample of a human subject, it means that said human subject has a low risk of developing an oral cancer.

For example, as shown in the example 4, the detection of the biochemical organic compounds of the group comprising: hexanitrile, 2,3-pentanedione, 3-methylthiophene and acetone in the volatile fraction of saliva of a human subject indicates that said human subject has a risk superior to 97% of developing an oral cancer, and is therefore predisposed to develop an oral cancer, or is developing an oral cancer. Therefore, in a preferred embodiment, the detection of at least hexanitrile, 2,3-pentanedione, 3-methylthiophene and acetone in the volatile fraction of saliva of a human subject indicates that said human subject has a risk superior to 97% of developing an oral cancer, and is therefore developing an oral cancer.

Also, the method of the present invention can rely on the detection of the level of expression of the compounds: 3-methyl-2-pentanone, methyl butanone, butanal, hexanal, hexanenitrile, 1-propanol 2-propanol, (cis) 1,2-dimethyl cyclopropane, phenol, and 2,3-butanedione in order to diagnose an oral cancer in a human subject, as demonstrated in the example 5.

In another embodiment, the present invention is drawn to a method of diagnosing a cancer in a human subject, wherein the detection of at least one biochemical organic compound in the volatile fraction of saliva of a human subject indicates that said human subject has a low risk of developing a cancer.

The compounds 2-methyl-2-butene (CAS number 513-35-9), 2-methyl-1-propene (CAS number 115-11-7) and (cis) 1,2-dimethyl cyclopropane (CAS number 930-18-7) are overexpressed in the volatile fraction of healthy human subject and are absent in the volatile fraction of patients suffering from oral cancer. Therefore, these compounds can serve as "healthy biochemical markers". The detection of at least one, preferably two of these biochemical organic compounds indeed indicates that the human subject has a low risk of being predisposed of being developing an oral cancer.

Therefore, in a preferred embodiment of the invention, the detection of at least one biochemical organic compound chosen in the group consisting of: 2-methyl-2-butene (CAS number 513-35-9), 2-methyl-1-propene (CAS number 115-11-7) and (cis) 1,2-dimethyl cyclopropane (CAS number 930-18-7) in the saliva of a human subject indicates that said human subject has a poor risk of developing an oral cancer, that is as a risk lower than 10%, preferably 5% of developing an oral cancer, as compared to the normal healthy population.

Moreover, the detection of particulate biochemical organic compounds such as benzaldehyde, acetone, and 2,3-pentanedione on a one hand, and the absence of other particulate biochemical compounds such as 2-methyl-2-butene, 2-methyl-1-propene, and/or (cis) 1,2-dimethyl cyclopropane on the other hand, enables to diagnose oral cancer with a high sensitivity (at least 93%, see example 4).

It is noteworthy that most of the above-mentioned biochemical compounds have never been identified so far in the saliva. Moreover, none of them have been related so far with cancer predisposition.

Therefore, the present invention is also drawn to the use of the detection of at least one compound chosen among: 2,3-pentanedione (CAS number 600-14-6), 3-methylthiophene (CAS number 616-44-4), acetone (CAS number 67-64-1), hexanenitrile (CAS number 628-73-9), benzaldehyde (CAS number 100-52-7), 3-methyl-2-pentanone (CAS number 565-61-7), 2,3-butanedione (CAS number 431-03-8), 2-propanol (CAS number 67-63-0), ethyl acetate (CAS number 141-78-6), 1-propanol (CAS number 71-23-8), hexanal (CAS number 66-25-1), 5-methyl-3-hexen-2-one (CAS number 5166-53-0), m-xylene (CAS number 108-38-3), p-xylene (CAS number 106-42-3), 2-methyl-2-butenal (E) (CAS number 497-03-0), 2-methyl-2-butene (CAS number 513-35-9), 2-methyl-1-propene (CAS number 115-11-7) and (cis) 1,2-dimethyl cyclopropane (CAS number 930-18-7), heptanal (CAS number 111-71-7), nonanal (CAS number 124-19-6), octanal (CAS number 124-13-0), cyclopentane methyl (CAS number 96-37-7), decane (CAS number 124-18-5), hexane (CAS number 110-54-3), nonane (CAS number 111-84-2), pentane 2,2,4-trimethyl (CAS number 540-84-1), benzene (CAS number 71-43-2), benzene ethyl (CAS number 100-41-4), styrene (CAS number 100-42-5), toluene (CAS number 108-88-3), butanoic acid 2-methyl-ethyl ester (CAS number 7452-79-1), 2-butanone (CAS number 78-93-3), 2-butanone 3-hydroxy (CAS number 513-86-0), acetophenone (CAS number 98-86-2), pentanal (CAS number 110-62-3), aniline (CAS number 62-53-3), furan 2-methyl (CAS number 534-22-5), decanal (CAS number 112-31-2), propanal 2-methyl (CAS number 78-84-2), butanal 3-methyl (CAS number 590-86-3), 2-propenal 2-methyl (CAS number 78-85-3), 1-butanol 3-methyl (CAS number 123-51-3), 2-butanol (CAS number 15892-23-6), 2,3-octanedione (CAS number 585-25-1), 2,3-pentanedione (CAS number 600-14-6), 2-octanone (CAS number 111-13-7), 2-heptanone (CAS number 110-43-0), 3-buten-2-one 3-methyl (CAS number 814-78-8), acetic acid (CAS number 64-19-7), butanoic acid 3-methyl-ethyl ester (CAS number 108-64-5), 1-hexene 3,5,5-trimethyl (CAS number 4316-65-8), 2-hexene 2,5,5-trimethyl (CAS number 40467-04-7), 1-propene 2-methyl (CAS number 115-11-7), methylcyclohexane (CAS number 108-87-2), cyclopropane 1,2-dimethyl (cis) (CAS number 930-18-7) in order to diagnose a cancer in a human subject.

In another aspect, the present invention is drawn to the use of the detection of the ten compounds: 3-methyl-2-pentanone, methylbutanone, butanal, hexanal, hexanenitrile, 1-propanol 2-propanol, (cis) 1,2-dimethyl cyclopropane, phenol, and 2,3-butanedione, in a diagnostic test for assessing a risk or a predisposition of oral cancer in a human subject.

In another aspect, the present invention is drawn to the use of the detection of hexanenitrile, 2,3-pentanedione, 3-methylthiophene and acetone for diagnosing a risk or a predisposition of oral cancer in a human subject.

In another aspect, the present invention is drawn to the use of the detection of the eleven compounds: butanal (CAS number 123-72-8), pentanal (CAS number 110-62-3), hexanal (CAS number 66-25-1), heptanal (CAS number 111-71-7), octanal (CAS number 124-13-0), nonanal (CAS number 124-19-6), 2-butanone (CAS number 78-93-3), 2-butanone 3-hydroxy- (CAS number 513-86-0), 2,3-butanedione (CAS number 431-03-8), benzaldehyde (CAS number 100-52-7), 1-propanol (CAS number 71-23-8) for diagnosing a risk or a predisposition of lung cancer in a human subject.

In another embodiment, the present invention is drawn to a kit to practice a method of diagnosing a predisposition of cancer, or a method of diagnosing a cancer, based on the volatile fraction of saliva, comprising:

a) A sterile device to collect a saliva sample, optionally containing a collect reagent
b) A preservation reagent,
c) At least one electronic sensor,
d) Optionally, a control molecular marker.

As mentioned before, the collect reagent is a dilution buffer which is preferably a citrate buffer.

The kit comprises a preservation reagent, which is preferably a buffer comprising a salt capable of reducing the vapour tension of volatile compounds without allowing the degradation of said compounds. This salt is preferably a salt such as guanidinum thiocyanate, and/or ammonium sulfate and/or sodium azide. This sodium azide is employed preferably at a concentration range between 20 mM and 6M, preferably between around 10 mM and 100 mM, more preferably around 40 mM. Other salts, such as guanidium thiocyanate and/or ammonium sulphate, are added at a concentration of 4M.

In one embodiment of the present invention, the preservation reagent is provided in a dry format in a sterile plastic tube under vacuum, which can draw up the saliva associated with the dilution buffer.

In the context of the invention, the device used to detect the organic compounds in the collected volatile fraction of saliva is an electronic sensor, for example electronic noses, JPL electronic noses, FET-type Bioelectronic noses, alpha mos). These technologies are now widely used and therefore known from the man skilled in the art (Cho S. M., Sensors and Actuators 2006).

Using specific electronic sensors for the identification of the targeted volatile compounds in a specific platform (electronic nose), the invention enables the user to perform a specific analysis platform or a point of care analysis usable in physician and dentists offices.

In one embodiment of the invention the control molecular markers are chosen among: 1-bromobutane, 1-bromobenzene and 1,4-dibromobenzene.

EXAMPLE 1

Stabilization of Crude Samples of Saliva

Raw saliva is collected with a medical device which makes easier the collection of a large volume of saliva (up to 2 ml). 4 ml of saliva extraction solution is then swallowed up to 2 minutes for collection of 2 ml of saliva.

The saliva extraction solution contains:
FD&C yellow n°5 (tartrazine)
Citrate buffer (39 mM)

The 2 ml of diluted saliva (in 4 ml) are then transferred in analysis tubes containing lyophilized sodium azide, for biomarker stabilization. The final sodium azide concentration is about 40 mM.

The tubes can be transported without control of temperature during 10 days before being analyzed.

EXAMPLE 2

Analysis of Organic Volatile Compounds in the Volatile Fraction of Saliva

It is known for a while that volatile compounds can be extracted from fluidic samples from oral cavity giving the possibility to explore the saliva as material to be analyzed for pathogenic diseases (Volozhin et al. Stomatologiia (mosk), 2001; 80(1):9-12).

In the present case, 1 ml of saliva solution is placed in a glass vial with 10 μL of the standard solution with 1 ppm of three (3) standards (1-bromobutane, 1-bromobenzene and 1.4-dibromobenzene; final solution with 1 ppm prepared in pure water).

The samples are placed at room temperature during at least 1 hour before analyzes. The sample is heated at 40° C. during 10 minutes then the extraction of the volatile compounds is carried out at 40° C., using a CAR/PDMS fiber (SPME fiber assembly CAR/PDMS of 75 μm (Supelco, Bellefont, Pa., USA)), during 30 minutes. Then the analysis was performed using GC/MS. The GC injection port temperature is 280° C. The injection of the volatile molecules in GC/MS is carried out by thermal desorption of the fiber at 280° C. The separation of the volatile compounds was led with a non-polar capillary column. The column temperature program was: initial temperature of 40° C. for 5 min, then increase at 3° C./min to 230° C. for 2 min. The mass spectra are measured by electronic impact at 70 e.V.

The identification of the volatile molecules is obtained by:
comparison of the experimental indices of retention to those of the internal data bank
comparison of the experimental spectra to those of the bank Wiley 275K.

The results of the exhaustive analysis of all the volatile organic compounds found in the volatile fraction of human saliva are reported on table 1.

TABLE 1

| Organic volatile compounds in volatile fraction of human saliva | |
|---|---|
| Molecule name | CAS number |
| 1,2-dichlorobenzene | 95-50-1 |
| disulfure de carbone | 137-26-8 |
| benzenecarboxylic acid | 65-85-0 |
| heptanoic acid | 111-14-8 |
| nonanoic acid | 112-05-0 |
| octanoic acid | 124-07-2 |
| pentanoic acid | 109-52-4 |
| 2-propenal, 2-methyl- | 78-85-3 |
| butanal | 123-72-8 |
| butanal, 3-methyl- | 590-86-3 |
| decanal | 112-31-2 |
| ethanal | 75-07-0 |
| heptanal | 111-71-7 |
| hexanal | 66-25-1 |
| hexanal, 2-ethyl- | 123-05-7 |
| nonanal | 124-19-6 |
| octanal | 124-13-0 |
| propanal, 2-methyl- | 78-84-2 |
| valeraldehyde, 4,4-dimethyl-2-methylene | 5375-28-0 |
| 7-oxabicyclo[4.1.0]heptane, 1-methyl- | 1713-33-3 |
| cyclopentane, methyl- | 96-37-7 |
| decane | 124-18-5 |
| hexane | 110-54-3 |
| methylcyclohexane | 108-87-2 |
| nonane | 111-84-2 |
| pentane, 2,2,4-trimethyl- | 540-84-1 |
| pentane, 2-methyl- | 107-83-5 |
| pentane, 3-methyl- | 96-14-0 |
| benzene | 71-43-2 |
| benzene, ethyl- | 100-41-4 |
| Butylated Hydroxytoluene | 128-37-0 |
| dehydro p-cymene | 1195-32-0 |
| dibenzofuran | 132-64-9 |
| m-xylene | 108-38-3 |
| o-xylene | 95-47-6 |
| p-cymene | 99-87-6 |
| styrene | 100-42-5 |
| toluene | 108-88-3 |
| 1-hexene, 3,5,5-trimethyl- | 4316-65-8 |
| 2-hexene, 2,5,5-trimethyl- | 40467-04-7 |
| butanoic acid, 2-methyl-, ethyl ester | 7452-79-1 |
| butanoic acid, 3-methyl-, ethyl ester | 108-64-5 |
| methyl thiolacetate | 1534-08-3 |

TABLE 1-continued

Organic volatile compounds in volatile fraction of human saliva

| Molecule name | CAS number |
|---|---|
| ethyl butanoate | 105-54-4 |
| ethyl propanoate | 105-37-3 |
| ethyl-N-methylcarbamate | 105-40-8 |
| methylacetate | 79-20-9 |
| 1,3-dioxolane, 2-methyl- | 497-26-7 |
| tert-butyl ethyl ether | 637-92-3 |
| bromoethane | 74-96-4 |
| bromomethane | 74-83-9 |
| chlorobutanol | 57-15-8 |
| dibromomethane | 74-95-3 |
| dichloromethane | 75-09-2 |
| heptane, 3-bromo- | 1974-05-6 |
| hexane, 1-chloro- | 544-10-5 |
| hexane, 3-chloro- | 2346-81-8 |
| phenol, 2-chloro-4-(1,1-dimethylpropyl)- | 98-28-2 |
| tribromomethane | 75-25-2 |
| 1H-pyrrole | 109-97-7 |
| 1H-pyrrole, 1-methyl- | 96-54-8 |
| 2-furfural | 98-01-1 |
| furan, 2-acetyl- | 1192-62-7 |
| furan, 2-ethyl- | 3208-16-0 |
| furan, 2-pentyl- | 3777-69-3 |
| furan, 3-methyl | 930-27-8 |
| furan, 5-methyl-2-propionyl- | 33978-70-0 |
| pyrazine | 290-37-9 |
| pyrazine, 2,5-dimethyl- | 123-32-0 |
| pyrazine, ethyl- | 13925-00-3 |
| pyrazine, methyl- | 109-08-0 |
| pyridine | 110-86-1 |
| 2-butenenitrile | 4786-20-3 |
| 2-piperidinone | 675-20-7 |
| 3-butenenitrile | 109-75-1 |
| benzene isocyanato | 103-71-9 |
| benzonitrile | 100-47-0 |
| butanenitrile, 3-methyl- | 625-28-5 |
| ethane, isocyano- | 624-79-3 |
| ethyl isocyanate | 109-90-0 |
| propanenitrile | 107-12-0 |
| propanenitrile, 2-methyl- | 78-82-0 |
| 1-hexanol | 111-27-3 |
| 1-hexanol, 2-ethyl- | 104-76-7 |
| 1-pentanol | 71-41-0 |
| 1-propanol, 2-methyl- | 78-83-1 |
| 2-butanol | 15892-23-6 |
| 2-butanol, 2-methyl- | 75-85-4 |
| 2-hexanol, 2,5-dimethyl- | 3730-60-7 |
| 2-pentanol, 2-methyl- | 590-36-3 |
| 2-propanol, 2-methyl- | 75-65-0 |
| 3-hexanol | 623-37-0 |
| ethanol | 64-17-5 |
| phenol | 108-95-2 |
| phenol, 4-(1,1-dimethylpropyl)- | 80-46-6 |
| skatole | 83-34-1 |
| 1,3-isobenzofuranedione | 85-44-9 |
| 2,3-octanedione | 585-25-1 |
| 2,4-pentanedione, 3-methyl- | 815-57-6 |
| 2,6-di-tert-butyl-p-benzoquinone | 719-22-2 |
| 2-butanone | 78-93-3 |
| 2-butanone, 3,3-dimethyl- | 75-97-8 |
| 2-butanone, 3-hydroxy- | 513-86-0 |
| 2-cyclohexen-1-one, 3,4,4-trimethyl- | 17299-41-1 |
| 2-cyclopenten-1-one, 2,3-dimethyl- | 1121-05-7 |
| 2-cyclopenten-1-one, 3-methyl- | 2758-18-1 |
| 2-hexanone, 3-methyl- | 2550-21-2 |
| 2-methyl-2-cyclopenten-1-one | 1120-73-6 |
| 3-heptanone | 106-35-4 |
| 3-hepten-2-one, 5-methyl- | 5090-16-4 |
| 3-octanone | 106-68-3 |
| 3-penten-2-one, 3-methyl- | 565-62-8 |
| 5-hepten-2-one, 6-methyl- | 110-93-0 |
| acetophenone | 98-86-2 |
| cyclohexanone | 108-94-1 |
| cyclopentanone, 2-methyl- | 1120-72-5 |
| cyclopentanone, 3-methyl- | 1757-42-2 |
| methylbutanone | 563-80-4 |
| p-methylacetophenone | 122-00-9 |
| disulfide, dimethyl | 624-92-0 |
| methanethiol | 74-93-1 |
| sulfone, dimethyl- | 67-71-0 |
| dimethyl sulfide | 75-18-3 |
| (Z)-caryophyllene | 118-45-0 |
| anethole (E) | 4180-23-8 |
| a-pinene | 80-56-8 |
| a-terpineol | 10482-56-1 |
| a-thujene | 2867-05-2 |
| b-bourbonene | 5208-59-3 |
| b-caryophyllene | 87-44-5 |
| b-pinene | 127-91-3 |
| camphene | 79-92-5 |
| carvone | 2244-16-8 |
| cis-p-menthan-3-one | 491-07-6 |
| dihydromyrcenol | 18479-59-9 |
| eucalyptol | 470-82-6 |
| limonene | 138-86-3 |
| m-mentha-6,8-diene | 1461-27-4 |
| neo-menthol | 491-01-0 |
| piperitone | 89-81-6 |
| p-menth-3-ene | 500-00-5 |
| trans-p-menthan-3-one | 89-80-5 |
| benzaldehyde | 100-52-7 |
| 2-octanone | 111-13-7 |
| 2-heptanone | 110-43-0 |
| 2,3-pentanedione | 600-14-6 |
| 2-pentanone, 3-methyl- | 565-61-7 |
| acetic acid | 64-19-7 |
| 3-hexanone | 589-38-8 |
| 1-propene, 2-methyl- | 115-11-7 |
| benzaldehyde, 2-methyl- | 529-20-4 |
| propanoic acid | 79-09-4 |
| butanoic acid | 107-92-7 |
| 3-pentanone, 2-methyl- | 565-69-5 |
| 2-pentanone 4,4-dimethyl- | 590-50-1 |
| ethyl acetate | 141-78-6 |
| thiophene, 3-methyl- | 616-44-4 |
| 2-pentanone | 107-87-9 |
| 2-hexanone | 591-78-6 |
| isovaleric acid | 503-74-2 |
| 2-pentanone, 4-methyl- | 108-10-1 |
| 2-butene, 2-methyl- | 513-35-9 |
| 1-propanol | 71-23-8 |
| 2-butenal, 2-methyl (E) | 497-03-0 |
| butanoic acid, 2-methyl- | 116-53-0 |
| 2-propanol | 67-63-0 |
| isobutyric acid | 79-31-2 |
| benzene, 2-methyl-1-propenyl- | 768-49-0 |
| hexanoic acid | 142-62-1 |
| acetone | 67-64-1 |
| pentanoic acid, 4-methyl- | 646-07-1 |
| cyclopropane, 1,2-dimethyl (cis) | 930-18-7 |
| p-cresol | 106-44-5 |
| 2,3-butanedione | 431-03-8 |
| 1-butanol, 3-methyl- | 123-51-3 |
| m-methyl acetophenone | 585-74-0 |
| 3-hexen-2-one, 5-methyl- | 5166-53-0 |
| indole | 120-72-9 |
| 3-hexen-2-one, 3,4-dimethyl- | 1635-02-5 |
| pentanal | 110-62-3 |
| 2-pentanol, 2,3-dimethyl- | 4911-70-0 |
| m-cymene | 535-77-3 |
| cyclohexanone | 108-94-1 |
| aniline | 62-53-3 |
| furan, 2-methyl- | 534-22-5 |
| 3-pentanone, 2,4 dimethyl - | 565-80-0 |
| 3-buten-2-one 3-methyl | 814-78-8 |
| hexanenitrile | 628-73-9 |
| heptanenitrile | 629-08-3 |
| pentane nitrile | 110-59-8 |
| butanenitrile | 109-74-0 |
| acrylonitrile | 107-13-1 |

From our experimental studies, 192 volatile molecules have been identified in the volatile fraction of human saliva (table 1). Principal volatile compounds identified in saliva are ketones, acids, aldehydes, alcohols and aromatic compounds.

Among these compounds, 57 volatile compounds have been preselected to be used has possible biomarkers discriminating factor for oral cancer early detection (table 2).

TABLE 2

Volatile compounds potentially indicative of oral cancer susceptibility

| Molecule name | CAS Number |
|---|---|
| benzaldehyde | 100-52-7 |
| 2-octanone | 111-13-7 |
| 2-heptanone | 110-43-0 |
| 2,3-pentanedione | 600-14-6 |
| 3-methyl-2-pentanone | 565-61-7 |
| acetic acid | 64-19-7 |
| 3-hexanone | 589-38-8 |
| 2-methyl-1-propene | 115-11-7 |
| 2-methyl-benzaldehyde | 529-20-4 |
| propanoic acid | 79-09-4 |
| butanoic acid | 107-92-7 |
| 2-methyl-3-pentanone | 565-69-5 |
| 4,4-dimethyl-2-pentanone | 590-50-1 |
| ethyl acetate | 141-78-6 |
| 3-methyl-thiophene | 616-44-4 |
| 2-pentanone | 107-87-9 |
| 2-hexanone | 591-78-6 |
| isovaleric acid | 503-74-2 |
| 4-methyl-2-pentanone | 108-10-1 |
| 2-methyl-2-butene | 513-35-9 |
| 1-propanol | 71-23-8 |
| (E) 2-methyl-2-butenal | 497-03-0 |
| 2-methyl-butanoic acid | 116-53-0 |
| 2-propanol | 67-63-0 |
| isobutyric acid | 79-31-2 |
| 2-methyl-1-propenyl-benzene | 768-49-0 |
| hexanoic acid | 142-62-1 |
| acetone | 67-64-1 |
| 4-methyl-pentanoic acid | 646-07-1 |
| (cis) 1,2-dimethyl cyclopropane | 930-18-7 |
| p-cresol | 106-44-5 |
| 2,3-butanedione | 431-03-8 |
| 3-methyl-1-butanol | 123-51-3 |
| m-methyl acetophenone | 585-74-0 |
| 5-methyl-3-hexen-2-one | 5166-53-0 |
| indole | 120-72-9 |
| 3,4-dimethyl-3-hexen-2-one | 1635-02-5 |
| pentanal | 110-62-3 |
| 2,3-dimethyl-2-pentanol | 4911-70-0 |
| m-cymene | 535-77-3 |
| cyclohexanone | 108-94-1 |
| aniline | 62-53-3 |
| 2-methyl-furan | 534-22-5 |
| 2,4 dimethyl-3-pentanone | 565-80-0 |
| 3-methyl-3-buten-2-one | 814-78-8 |
| hexanenitrile | 628-73-9 |
| heptanenitrile | 629-08-3 |
| pentane nitrile | 110-59-8 |
| butanenitrile | 109-74-0 |
| 3-méthyl-2-pentanone | 565-61-7 |
| methylbutanone | 563-80-4 |
| butanal | 123-72-8 |
| hexanal | 66-25-1 |
| phenol | 108-95-2 |
| m-xylene | 108-38-3 |
| p-xylene | 106-42-3 |
| ethanal | 75-07-0 |
| benzene | 71-43-2 |
| acrylonitrile | 107-13-1 |

According to our results, at least 19 of these 57 compounds are indeed correlated with oral cancer, as shown below.

EXAMPLE 3

Quantification of the Identified Volatile Compounds in Cancer/Healthy Patients

The quantification of the volatile compounds is made by comparison with standard controls that have been added in the preservation buffer at the beginning of the experiment. In this case, the followings molecular standards have been used:
1-bromobutane (CAS number 109-65-9)
1-bromobenzene (CAS number 108-86-1)
1,4-dibromobenzene (CAS number 106-37-6)

TABLE 3

Particular biomarkers indicative of oral cancer predisposition

| Biomarker name | Overexpression in oral cancer population | Overexpression in normal population |
|---|---|---|
| 2,3-pentanedione | 6.00 X | |
| 3-methyltiophene | 1.50 X | |
| acetone | 2.30 X | |
| hexanitrile | 3.00 X | |
| benzaldehyde | 1.80 X | |
| 3-methyl-2-pentanone | 2.10 X | |
| 2,3-butanedione | 4.40 X | |
| 2-propanol | 2.80 X | |
| ethyl acetate | 3.90 X | |
| 1-propanol | 1.90 X | |
| hexanal | 1.60 X | |
| 5-methyl-3-hexen-2-one | 1.70 X | |
| m- and p-xylene | 1.50 X | |
| 2-methyl-2-butenal (E) | 1.90 X | |
| 2-methyl-2-butene | | 2.00 X |
| 2-methyl-1-propene | | 3.30 X |
| (cis) 1,2-dimethyl cyclopropane | | 1.70 X |

It has been concluded from these data that the "detection" of a certain volatile compound in a saliva sample of a patient means that said sample contains at least 1.5 fold the amount of said compound in the normal population.

EXAMPLE 4

Statistical Analysis of the Presence of Biochemical Organic Compounds in the Saliva of Oral Cancer Patient Vs Healthy Individuals Software STATISTICA version 8.0 of StatSoft France (2007) is used for data analysis. The significances of the differences between the groups were tested by from Factorial Discriminating Analysis (FDA). Thus the similarities or the differences of the samples can be visualized graphically.

The identification of the volatile molecules is obtained by:
Comparison of the experimental indices of retention to those of the internal data bank,
comparison of the experimental spectra to those of the bank Wiley 275K and NIST 2.0d, built April 2005.

Statistical Model 1

Total population tested is 45 human subjects from two distinctive environmental geographic areas. Oral cancer population is confirmed by visual diagnostics performed by an anticancer center.

The statistical analyzes were carried out on 109 volatile compounds. Abundances of the molecules in each sample were reported to abundances of the 3 internal standards analyzed with saliva. The principal volatile compounds identified in saliva are ketones, acids, aldehydes, alcohols and aromatic compounds. All the samples have a strong abundance in hydrazoic acid coming directly from the buffer solution of conservation.

On the 108 volatile compounds, 49 are significant to separate the group "tumor" from the reference group. A discriminating factorial analysis on these variables makes it possible to classify well 97.78% of the samples with 4 volatile compounds: the hexanenitrile, the 2,3-pentanedione, 3-methylthiophene and acetone. Only 1 false-positive have been detected with the statistical model 1.

Statistical Model 2

Total population tested is 45 human subjects from two distinctive environmental geographic areas. Oral cancer population is confirmed by visual diagnostics performed by a specialized anticancer center.

The statistical analyzes were carried out on 108 volatile compounds. Abundances of the molecules in each sample were reported to abundances of the 3 internal standards analyzed with saliva. The principal volatile compounds identified in saliva are ketones, acids, aldehydes, alcohols and aromatic compounds. All the samples have a strong abundance in hydrazoic acid coming directly from the buffer solution of conservation.

All nitriles volatile compounds have been removed from the statistical model number 2. For this study, the 10 made up "nitriles" were not taken into account.

From the 98 remaining volatile compounds, an ANOVA test according to the factor "tumor" showed that 45 components are significant to separate the group "tumor" from the reference group.

A discriminating factorial analysis on these variables makes it possible to classify well 93.33% of the samples with 4 volatile compounds: benzaldehyde, acetone, the 2,3-pentanedione and 2-methyl-2-butene. The first 3 molecules are side of the group "tumor" and the 2-methyl-2-butene on the side of the control group. 3 false-negatives and no false positive have been detected with the statistical model 2.

To conclude, this study highlights the tight link existing between 14 organic compounds (namely hexanenitrile, the 2,3-pentanedione, 3-methylthiophene, 2-methyl-2-butylene, 3-methyl-2-pentanone, 2,3-butanedione, 2-propanol, ethyl acetate, 1-propanol, hexanal, 5-methyl-3-hexen-2-one, m-xylene, p-xylene, 2-methyl-2-butenal (E)) and oral cancer in human. It is noteworthy that none of them have ever been found in exhaled breath (Mashir A, Advanced Powder Technology, 2009) or being associated to oral cancer.

EXAMPLE 5

Diagnostic Test Based on the Ratios of Specific Organic Molecules

Software STATISTICA version 8.0 of StatSoft France (2007) is used for data analysis. The significances of the differences between the groups were tested by Factorial Discriminating Analysis (FDA). Thus the similarities or the differences of the samples can be visualized graphically.

Tested Population

Total population tested is 52 human subjects from two distinctive environmental geographic areas. Oral cancer population is confirmed by visual diagnostics performed by a specialized anticancer center.

The following volatile organic compounds are used in the diagnostic test:
3-methyl-2-pentanone (CAS number: 565-61-7)
Methylbutanone (CAS number: 563-80-4)
2.4-dimethyl-3-pentanone (CAS number: 565-80-0)
Benzene (CAS number: 71-43-2)
Phenol (CAS number: 108-95-2)
2.3-butanedione (CAS number: 431-03-8)
5-methyl-3-hexen-2-one (CAS number: 5166-53-0)
2-methyl-1-propene (CAS number: 115-11-7)
Butanal (CAS number: 123-72-8)
Hexanal (CAS number: 66-25-1)
2-propanol (CAS number: 67-63-0)
Ethyl acetate (CAS number: 141-78-6)
Hexanenitrile (CAS number: 628-73-9)
1-propanol (CAS number: 71-23-8)
(cis) 1,2-dimethyl-cyclopropane (CAS number: 930-18-7)
m- and p-xylene (CAS number: 108-38-3 and CAS number: 106-42-3)
(E) 2-methyl-2-butenal (CAS number: 497-03-0)
3-methyl-thiophene (CAS number: 616-44-4)
Ethanal (CAS number: 75-07-0)

The median values by group were calculated for the following ratios:
3-methyl-2-pentanone/methyl butanone
2.4-dimethyl-3-pentanone/benzene
phenol/2,3-butanedione
5-methyl-3-hexen-2-one/2-methyl-1-propene
butanal/hexanal
2-propanol/ethyl acetate
hexanenitrile/1-propanol
2-propanol/(cis) 1.2-dimethyl cyclopropane
m-xylene/2-methyl-2-butenal
3-methyl-2-pentanone/3-methyl-thiophene,
2,3-butanedione/ethanal The statistical method used is FDA (Factorial Discrimination Analysis).

The median values by group were calculated for each of the ratios.

The 5 followings were found to be statistically significative of oral cancer patient group or control group:
1) 3-methyl-2-pentanone/methyl butanone (R1)
2) Butanal/hexanal (R56)
3) Hexanenitrile/1-propanol (R260)
4) 2-propanol/(cis) 1,2 dimethyl cyclopropane (R266)
5) Phenol/2,3 butanedione (R269).

Among these ratios, 2 were found to be reproducibly correlated with healthy subjects, and three were indicative of oral cancer suffering patients (table 4).

TABLE 4

Median values for the 5 ratios correlated with oral cancer or healthiness

| | R1 3-methyl-2-pentanone/ methyl butanone | R56 Butanal/ hexanal | R260 Hexanenitrile/ 1-propanol | R266 2-propanol/ (cis) 1,2-dimethyl cyclopropane | R269 Phenol/2,3-butanedione |
|---|---|---|---|---|---|
| Average healthy | 0.182 | 0.223 | 0.040 | 2.939 | 0.696 |
| Average Oral Cancer | 0.357 | 0.138 | 0.089 | 9.359 | 0.217 |

The 3 ratios R1 (3-methyl-2-pentanone/methyl butanone), R260 (Hexanenitrile/1-propanol) and R266(Phenol/2,3-butanedione) are of the side of the oral cancer group group and the values are respectively 1.96; 2.24 and 3.18 times higher in this group than in the healthy group.

The 2 ratios R56 (Butanal/hexanal) and R269 (Phenol/2,3-butanedione) are of the side of the healthy group and are respectively 1.62 and 3.21 higher in this group than in the oral cancer group.

The absolute limiting values of the ratios permitting to classify the patients in a potential "oral cancer group" are given in table 5:

TABLE 5

Absolute limiting ratio values permitting to classify the patients

| Report/ratio | Condition so that the sample is "oral cancer risk" | Nb samples corresponding to the ratio |
|---|---|---|
| 3-methyl-2-pentanone/methyl butanone | >0.344 | 17 |
| Butanal/hexanal | <0.11 | 10 |
| Hexanenitrile/1-propanol | >0.167 | 3 |
| 2-propanol/(cis) 1,2-dimethyl cyclopropane | >10.33 | 9 |
| Phenol/2,3-butanedione | <0.005 | 4 |

To classify the samples it is necessary to apply the following formula (from the FDA statistical method) taking into account all these 5 ratios (linear combination of the 5 variable ratios):

Factor $X = 1.8277 - 7.3472*R1 - 0.125*R266 - 14.2293*R260 + 1.2050*R269 + 8.883*R56$ If factor $X \leq 0.6$, the sample is classified in the Oral Cancer Risk Population If factor $X > 0.6$, the sample is classified healthy Therefore, the method of the invention, based on:
i) the recovery of the volatile fraction of the saliva of a human subject,
ii) the quantification of ten biochemical organic compounds (3-methyl-2-pentanone, methyl butanone, Butanal, hexanal, Hexanenitrile, 1-propanol 2-propanol, (cis) 1,2-dimethyl cyclopropane, phenol, and 2,3-butanedione) in said volatile fraction,
iii) calculation of the ratios R1, R266, R260, R269 and R56 as mentioned above,
iv) calculation of said factor X and its comparison with the threshold 0.6, enables the man skilled in the art to prognose and/or diagnose an oral cancer in said human subject.

The analysis of the ratios between the organic compounds: 3-methyl-2-pentanone/methyl butanone, Butanal/hexanal, Hexanenitrile/1-propanol 2-propanol/(cis) 1,2-dimethyl cyclopropane, and Phenol/2,3-butanedione in the volatile fraction of the saliva of a human subject permits to obtain a highly sensitive test of predisposition of oral cancer (98.077% sensitivity; 1 false-positive) (FIG. 1).

EXAMPLE 6

Quantification of the Identified Volatile Compounds in Lung Cancer/Healthy Patients The quantification of the volatile compounds is made by comparison with standard controls that have been added in the preservation buffer at the beginning of the experiment. In this case, the followings molecular standards have been used:
1-bromobutane (CAS number 109-65-9)
1-bromobenzene (CAS number 108-86-1)
1,4-dibromobenzene (CAS number 106-37-6)

From our experimental studies, 192 volatile molecules have been identified in the volatile fraction of human saliva (table 1). Principal volatile compounds identified in saliva are ketones, acids, aldehydes, alcohols and aromatic compounds.

Among these compounds, 57 volatile compounds have been preselected to be used has possible biomarkers discriminating factor for cancer early detection (table 2).

On the 57 volatile compounds, 47 volatile compounds have been preselected to be used has possible biomarkers discriminating factor for lung cancer early detection (table 6). These 47 volatil compounds are significant to separate the group "tumor" from the reference group.

TABLE 6

Volatile compounds potentially indicative of lung cancer susceptibility

| Molecule name | CAS number |
|---|---|
| butanal | 123-72-8 |
| heptanal | 111-71-7 |
| hexanal | 66-25-1 |
| nonanal | 124-19-6 |
| octanal | 124-13-0 |
| cyclopentane, methyl- | 96-37-7 |
| decane | 124-18-5 |
| hexane | 110-54-3 |
| nonane | 111-84-2 |
| pentane, 2,2,4-trimethyl- | 540-84-1 |
| benzene | 71-43-2 |
| benzene, ethyl- | 100-41-4 |
| styrene | 100-42-5 |
| toluene | 108-88-3 |
| butanoic acid, 2-methyl-, ethyl ester | 7452-79-1 |
| 2-butanone | 78-93-3 |
| 2-butanone, 3-hydroxy- | 513-86-0 |
| acetophenone | 98-86-2 |
| benzaldehyde | 100-52-7 |
| ethyl acetate | 141-78-6 |
| 2-butene, 2-methyl- | 513-35-9 |
| 1-propanol | 71-23-8 |
| acetone | 67-64-1 |
| 2,3-butanedione | 431-03-8 |
| pentanal | 110-62-3 |
| aniline | 62-53-3 |
| furan, 2-methyl- | 534-22-5 |
| decanal | 112-31-2 |
| propanal, 2-methyl- | 78-84-2 |
| butanal, 3-methyl- | 590-86-3 |
| 2-propenal, 2-methyl- | 78-85-3 |
| 2-butenal, 2-methyl (E) | 497-03-0 |
| 1-butanol, 3-methyl- | 123-51-3 |
| 2-propanol | 67-63-0 |
| 2-butanol | 15892-23-6 |
| 2,3-octanedione | 585-25-1 |
| 2,3-pentanedione | 600-14-6 |
| 2-octanone | 111-13-7 |
| 2-heptanone | 110-43-0 |
| 3-buten-2-one 3-methyl | 814-78-8 |
| acetic acid | 64-19-7 |
| butanoic acid, 3-methyl-, ethyl ester | 108-64-5 |
| 1-hexene, 3,5,5-trimethyl- | 4316-65-8 |
| 2-hexene, 2,5,5-trimethyl- | 40467-04-7 |
| 1-propene, 2-methyl- | 115-11-7 |
| methylcyclohexane | 108-87-2 |
| cyclopropane, 1,2-dimethyl (cis) | 930-18-7 |

According to our results, at least 11 of these 47 compounds are indeed correlated with lung cancer. A discriminating factorial analysis on these variables makes it possible to classify the samples with 11 volatile compounds being particularly relevant, as shown below (table 7).

TABLE 7

Particular biomarkers present and overexpressed in saliva indicative of lung cancer

| Biomarker name | Overexpression in lung cancer population |
|---|---|
| butanal | 1.5 |
| pentanal | 1.5 |
| hexanal | 1.5 |
| heptanal | 1.5 |
| octanal | 1.5 |
| nonanal | 1.5 |
| 2-butanone | 2.0 |
| 2-butanone, 3-hydroxy- | 2.0 |
| 2,3-butanedione | 2.0 |
| benzaldehyde | 1.5 |
| 1-propanol | 1.9 |

It has been concluded from these data that the "detection" of a certain volatile compound in a saliva sample of a patient means that said sample contains at least 1.5 fold the amount of said compound in the normal population.

The invention claimed is:

1. A method of diagnosing an oral or lung cancer in a human subject, comprising:
   collecting a crude saliva sample from said human subject and stabilizing the saliva sample with the addition of salt at a concentration range between 20 mM to 6 M;
   analyzing said saliva sample for biochemical organic compounds by gas chromatography coupled to mass spectrometry, wherein said compounds have been extracted from the sample by heating the sample for at least 10 minutes at 40° C. and by extracting with Solid-Phase Microextraction with a CAR/PDMS fiber;
   determining whether at least one compound selected from group (A) consisting of: 2,3-pentanedione, 3-methyltiophene, acetone, hexanenitrile, benzaldehyde, 3-methyl-2-pentanone, 2,3-butanedione, 2-propanol, ethyl acetate, 1-propanol, hexanal, 5-methyl-3-hexen-2-one, m-xylene, p-xylene, 2-methyl-2-butenal, butanal, pentanal, heptanal, octanal, nonanal, 2-butanone, and 3-hydroxy-2-butanone is overexpressed in the saliva sample, and/or
   determining whether at least one compound selected from group (B) consisting of: 2-methyl-2-butene, 2-methyl-1-propene, and (cis) 1,2 dimethyl-cyclopropane is underexpressed in the saliva sample; and
   diagnosing said subject as having a risk of developing oral or lung cancer if at least one of said compound from group (A) is overexpressed and/or at least one of said compound from group (B) is underexpressed, when compared to a mean expression level of said compound in the saliva of a normal healthy human population.

2. The method according to claim 1, wherein the crude saliva is stabilized with a solution comprising a salt selected from the group consisting of guanidium thiocyanate, ammonium sulfate, and sodium azide.

3. The method according to claim 2, wherein the overexpression of said at least one compound is at least 1.5 fold greater than the mean expression level of said compound in the saliva of a normal healthy human population.

4. The method according to claim 2, comprising:
   a) collecting the sample of crude saliva of said human subject in a sterile device,
   b) stabilizing said sample by adding a solution comprising a salt selected from the group consisting of guanidinum thiocyanate, ammonium sulfate, and sodium azide,
   c) extracting a volatile fraction from said stabilized sample by heating the sample for at least 10 minutes at 40° C. and extracting with the solid-phase microextraction (SPME) with a CAR/PDMS fiber to collect the volatile fraction, and
   d) analyzing said extracted saliva sample for the biochemical organic compounds by the gas chromatography coupled to mass spectrometry.

5. The method according to claim 1, wherein the overexpression of said at least one compound is defined as at least 1.5 fold greater than the mean expression level of said compound in the saliva of a normal healthy human population.

6. The method according to claim 1, comprising:
   a) collecting the sample of crude saliva of said human subject in a sterile device,
   b) stabilizing said sample by adding a solution comprising a salt selected from the group consisting of guanidinum thiocyanate, ammonium sulfate, and sodium azide,
   c) extracting a volatile fraction from said stabilized sample by heating the sample for at least 10 minutes at 40° C. and extracting with the solid-phase microextraction (SPME) with a CAR/PDMS fiber to collect the volatile fraction, and
   d) analyzing said extracted saliva sample for the biochemical organic compounds by the gas chromatography coupled to mass spectrometry.

7. The method according to claim 1, wherein detecting the overexpression of at least one compound selected from the group consisting of: 2,3-pentanedione, 3-methylthiophene, acetone, hexanenitrile, benzaldehyde, 3-methyl-2-pentanone, 2,3-butanedione, 2-propanol, ethyl acetate, 1-propanol, hexanal, 5-methyl-3-hexen-2-one, m-xylene, p-xylene, and 2-methyl-2-butenal indicates that said human subject has a high risk of developing an oral cancer or is developing an oral cancer.

8. The method according to claim 1, wherein detecting the overexpression of at least one compound selected from the group consisting of: butanal, pentanal, hexanal, heptanal, octanal, nonanal, 2-butanone, 3-hydroxy-2-butanone, 2,3 butanedione, benzaldehyde, and 1-propanol indicates that said human subject has a high risk of developing a lung cancer or is developing a lung cancer.

9. The method according to claim 1, wherein the cancer is oral cancer,
   the at least one biochemical organic compound comprises hexanenitrile, 2,3-pentanedione, 3-methylthiophene and acetone, and
   the overexpression of each of the hexanenitrile, 2,3-pentanedione, 3-methylthiophene and acetone is indicative of the presence of oral cancer in the human subject.

10. The method according to claim 1, wherein the cancer is oral cancer,
    the at least one biochemical organic compound comprises benzaldehyde, acetone, 2,3-pentanedione, and 2-methyl-2-butene, and
    the overexpression of each of benzaldehyde, acetone, and 2,3-pentanedione, and the underexpression of 2-methyl-2-butene, is indicative of the presence of oral cancer in the human subject.

* * * * *